US010631617B2

(12) United States Patent
Lucet-Levannier et al.

(10) Patent No.: US 10,631,617 B2
(45) Date of Patent: *Apr. 28, 2020

(54) METHOD FOR DELIVERING COSMETIC ADVICE

(71) Applicant: L'OREAL, Paris (FR)

(72) Inventors: Karine Lucet-Levannier, Rueil-Malmaison (FR); François Christiaens, Saint Maur des Fosses (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/244,737

(22) Filed: Jan. 10, 2019

(65) Prior Publication Data

US 2019/0183233 A1    Jun. 20, 2019

Related U.S. Application Data

(63) Continuation of application No. 14/368,230, filed as application No. PCT/IB2012/057558 on Dec. 20, 2012, now Pat. No. 10,213,007.

(Continued)

(30) Foreign Application Priority Data

Dec. 23, 2011   (FR) ...................................... 11 62435

(51) Int. Cl.
*G06K 9/00*        (2006.01)
*A45D 44/00*      (2006.01)
(Continued)

(52) U.S. Cl.
CPC .......... *A45D 44/005* (2013.01); *A61B 5/0077* (2013.01); *A61B 5/0082* (2013.01);
(Continued)

(58) Field of Classification Search
CPC .. A45D 44/005; A61B 5/0077; A61B 5/0082; A61B 5/1034; A61B 5/441
See application file for complete search history.

(56) References Cited

U.S. PATENT DOCUMENTS 4,428,050 A *  1/1984  Pellegrino ................ A61N 5/00
                                                          250/372
4,730,260 A *  3/1988  Mori .................... G02C 13/003
                                                          345/632

(Continued)

FOREIGN PATENT DOCUMENTS

CN    1377002 A    10/2002
CN    1750773 A    3/2006
(Continued)

OTHER PUBLICATIONS

Oct. 7, 2016 Office Action issued in Japanese Patent Application No. 2014-548316.
(Continued)

*Primary Examiner* — Sean T Motsinger
(74) *Attorney, Agent, or Firm* — Oliff PLC

(57) ABSTRACT

Cosmetic method in which: a) a color is acquired from a region of the body of an individual, by using a device equipped with a color camera and by placing a color reference chart in the field of said camera during the acquisition; and b) using the device, and the color acquired in a), and optionally knowledge of the tanning pathways of various skin colors, at least one indication is delivered concerning skin type and/or at least one indication is delivered concerning at least one skin color obtainable by the individual via the pigmentation or depigmentation process and/or at least one indication is delivered concerning photoprotection and/or application or administration of a product intended to temporarily modify the color of the skin.

17 Claims, 6 Drawing Sheets

Related U.S. Application Data

(60) Provisional application No. 61/645,859, filed on May 11, 2012, provisional application No. 61/592,405, filed on Jan. 30, 2012.

(51) Int. Cl.
 *A61B 5/00* (2006.01)
 *A61B 5/103* (2006.01)

(52) U.S. Cl.
 CPC ............ *A61B 5/1034* (2013.01); *A61B 5/441* (2013.01); *A45D 2044/007* (2013.01)

(56) References Cited

U.S. PATENT DOCUMENTS

| | | | | |
|---|---|---|---|---|
| 5,365,068 | A * | 11/1994 | Dickerson | A61N 5/06 250/372 |
| 6,018,381 | A * | 1/2000 | Vanderbrook | G03B 27/73 355/38 |
| 6,373,573 | B1 * | 4/2002 | Jung | A61B 5/0075 347/19 |
| 6,452,188 | B1 * | 9/2002 | Chubb | A61B 5/0059 250/338.1 |
| 6,936,824 | B2 * | 8/2005 | Takada | A61B 5/0059 250/372 |
| 8,044,363 | B2 * | 10/2011 | Ales | A61B 5/0059 250/336.1 |
| 8,688,268 | B2 * | 4/2014 | Samain | A45D 44/005 700/233 |
| 9,442,973 | B1 * | 9/2016 | Tuan | G06Q 30/0631 |
| 2002/0115926 | A1 * | 8/2002 | Takada | A61B 5/0059 600/407 |
| 2003/0064350 | A1 * | 4/2003 | Rubinstenn | A45D 44/005 434/99 |
| 2003/0067545 | A1 | 4/2003 | Giron et al. | |
| 2004/0131996 | A1 | 7/2004 | Ortiz-Valero et al. | |
| 2006/0036135 | A1 * | 2/2006 | Kern | A61B 5/1034 600/300 |
| 2007/0058858 | A1 * | 3/2007 | Harville | A45D 44/005 382/165 |
| 2007/0058860 | A1 * | 3/2007 | Harville | G06K 9/00234 382/167 |
| 2007/0064119 | A1 * | 3/2007 | Komiya | H04N 9/045 348/222.1 |
| 2008/0008370 | A1 * | 1/2008 | Chio | A61B 5/441 382/128 |
| 2008/0107320 | A1 * | 5/2008 | Cotton | A61B 5/0059 382/131 |
| 2008/0265170 | A1 * | 10/2008 | Ales | A61B 5/0059 250/372 |
| 2008/0304741 | A1 * | 12/2008 | Brunner | G06K 9/00456 382/168 |
| 2009/0025747 | A1 * | 1/2009 | Edgar | A45D 44/005 132/320 |
| 2009/0196496 | A1 * | 8/2009 | Kalla | A45D 44/005 382/165 |
| 2009/0245603 | A1 * | 10/2009 | Koruga | A45D 44/00 382/128 |
| 2010/0185064 | A1 * | 7/2010 | Bandic | A61B 5/0059 600/306 |
| 2010/0226531 | A1 * | 9/2010 | Goto | G06T 11/00 382/103 |
| 2011/0009374 | A1 * | 1/2011 | Keller | A61K 9/0014 514/179 |
| 2011/0014137 | A1 * | 1/2011 | Talalay | A61K 31/26 424/59 |
| 2011/0064307 | A1 | 3/2011 | Kalla et al. | |
| 2011/0202480 | A1 * | 8/2011 | Maes | A61B 5/441 705/500 |
| 2011/0247718 | A1 * | 10/2011 | Samain | A45D 44/005 141/1 |
| 2012/0300049 | A1 * | 11/2012 | Clemann | A45D 44/005 348/77 |
| 2012/0300050 | A1 * | 11/2012 | Korichi | A61B 5/0059 348/77 |
| 2014/0229192 | A1 * | 8/2014 | Zastrow | A61B 5/1032 705/2 |
| 2014/0368629 | A1 * | 12/2014 | Lucet-Levannier | A45D 44/005 348/77 |
| 2014/0378810 | A1 * | 12/2014 | Davis | G06F 16/245 600/407 |
| 2015/0338272 | A1 * | 11/2015 | Rastegar | G01J 1/0271 250/372 |

FOREIGN PATENT DOCUMENTS

| | | | |
|---|---|---|---|
| CN | 101754701 A | 6/2010 | |
| DE | 3 137 326 A1 | 3/1983 | |
| DE | 196 12 531 A1 | 10/1997 | |
| FR | 2 937 511 A1 | 4/2010 | |
| JP | S58-127633 A | 7/1983 | |
| JP | 2001-353129 A | 12/2001 | |
| JP | 2002-015068 A | 1/2002 | |
| JP | 2006-071581 A | 3/2006 | |
| JP | 2010-161591 A | 7/2010 | |
| JP | 2010-533537 A | 10/2010 | |
| WO | 2008/038135 A2 | 4/2008 | |
| WO | 2008/108760 A1 | 9/2008 | |
| WO | 2009/013687 A2 | 1/2009 | |
| WO | WO-2009013687 A2 * | 1/2009 | ........... A45D 44/005 |
| WO | 2010/046883 A1 | 4/2010 | |
| WO | WO-2010046883 A1 * | 4/2010 | ........... A45D 44/005 |
| WO | WO-2010046884 A1 * | 4/2010 | ........... A45D 44/005 |

OTHER PUBLICATIONS

Jan. 16, 2017 Office Action issued in European Application No. 12 824 713.7.
Chardon et al., "Skin colour typology and suntanning pathways," International Journal of Cosmetic Science, 1991, pp. 191-208, vol. 13.
May 10, 2013 International Search Report issued in International Application No. PCT/IB2012/057558.
May 10, 2013 Written Opinion isued in International Application No. PCT/IB2012/057558.
Jun. 14, 2018 Office Action issued in U.S. Appl. No. 14/368,230.
Oct. 5, 2017 Office Action issued in U.S. Appl. No. 14/368,230.
Apr. 3, 2017 Office Action issued in U.S. Appl. No. 14/368,230.
Sep. 22, 2016 Office Action issued in U.S. Appl. No. 14/368,230.
Del Bino et al., "Relationship between skin response to ultraviolet exposure and skin color type," Pigment Cells Res., 2006, pp. 606-614, vol. 19.

* cited by examiner

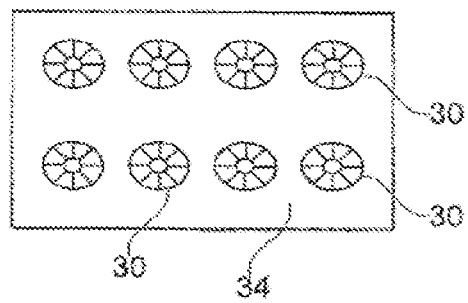
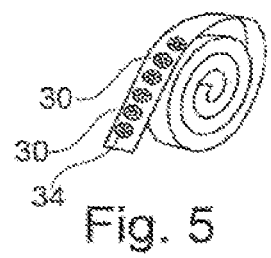
Fig. 4
Fig. 5
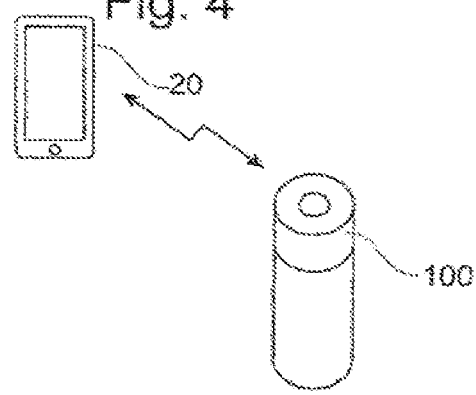
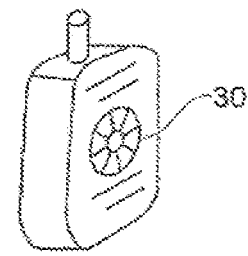
Fig. 10
Fig. 3
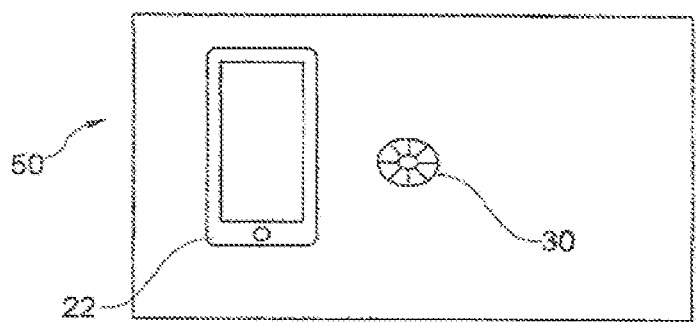
Fig. 3a

METHOD FOR DELIVERING COSMETIC ADVICE

This is a Continuation of application Ser. No. 14/368,230 filed Jun. 23, 2014, which in turn is a National Stage Application of PCT/IB2012/057558 filed Dec. 20, 2012, and claims the benefit of French Application No. 1162435 filed Dec. 23, 2011, U.S. Provisional Application No. 61/592,405 filed Jan. 30, 2012 and U.S. Provisional Application No. 61/645,859 filed May 11, 2012. The entire disclosure of the prior applications is hereby incorporated by reference herein its entirety.

The present invention relates to skin pigmentation and the provision of advice regarding the photoprotection to be applied and/or to individual skin colors obtainable via tanning.

The idea of classifying various skin types according to their sensitivity to solar radiation has been around for a long time. Thus, as early as 1977 the Fitzpatrick classification differentiated between six phototypes I to VI ranging from Caucasian skin that does not tan to highly pigmented African skin.

Subsequently, a more precise classification was suggested by A. Chardon, I. Cretois, C. Hourseau in *Skin color typology and suntanning pathways* International Journal of Cosmetic Science 13, 191-208 (1991). This classification is based on knowledge of the CIE (1976) L*a*b* color coordinates of the skin and on the calculation of the individual typology angle (ITA°)=(arc tan((L*−50)/b*))*180/pi. According to this classification, a high ITA° angle characterizes a light skin and a low angle a more pigmented skin.

It is also known that there is a relationship between the skin color obtained while tanning and the skin type. A. Chardon demonstrated, in the above article, that it is possible to define tanning pathways, i.e. to determine the change in the L* and b* components for a given skin type under increasing sun exposure.

Moreover, the dangers of exposure to the sun are now well known and there is a tendency towards more frequent use of photoprotective compositions. However, the user is confronted, when they decide to use a photoprotective composition and if they would like to tan rapidly, with the problem of choosing the sun protection factor.

Specifically, exposure to the sun results, except for the lightest skin, in the production of melanin, which makes the skin less sensitive to subsequent exposure. If the user employs a photoprotective composition with too high a factor, their skin will tan very slowly or they will not tan at all and the individual will possibly be unhappy with how little they have tanned, especially when they have a limited time to spend exposed to the sun, which is the case, for example, when on vacation. If, in contrast, the user employs a photoprotective composition with too low a factor, they run the risk of getting sunburnt and of no longer being able to expose themselves to the sun for a certain period of time, which may force them to abandon certain activities.

To help the consumer make a choice, it is known to inform them, on the day or beforehand, of the UV radiation strength in order to encourage them to use a photoprotective composition with a higher factor when the UV radiation is stronger.

However, knowing the UV index does not completely simplify the choice of photoprotective composition to apply, because other factors need to be taken into account, such as phototype and the degree of tanning already obtained.

Devices, equipped with a UV-radiation sensor, have also been proposed in order to provide the user with this information at any moment.

The Applicant has moreover proposed in publication FR 2 937 511 to equip a bottle comprising a plurality of compartments with an adjustment system and a UV-radiation sensor, in order to automatically deliver, to the user, a photoprotective composition having a protection index suited to the ambient UV radiation.

The Applicant has also proposed, in application US 2011/0247718 A1, a bottle equipped with a data receiver allowing a mixing system to be automatically set to deliver a photoprotective composition having the factor considered to correspond best to the needs of the user.

These proposals are not completely satisfactory solutions to the problem of choosing the protection factor because, on the one hand, the proposed systems are relatively complex and expensive, and on the other hand, they still do not accurately take the level of tan of the individual into account.

Other systems exist, which carry out measurements on the skin in order to give advice on the protection to be used, especially depending on the time exposed to the sun and on the sensitivity of the skin. Thus, U.S. Pat. No. 8,044,363 discloses a portable device for detecting UV which includes a reflectometer or colorimeter for measuring the skin type. Several measurements may be carried out on the body in order to calculate an average or to retain the measurement that is representative of the greatest sensitivity to the sun.

Such a device does not inform the user of the individual skin color that they are liable to obtain by tanning. In addition, such a device having a specific use may prove to be relatively expensive to manufacture, thereby limiting its use.

Finally, other existing systems, in order to give advice, use a questionnaire to determine skin type, the answers to this questionnaire sometimes being quite subjective or imprecise as they, for example, relate to childhood memories.

US 2003/0067545 A1 discloses a spherical chamber containing apertures in which a person places their face. The chamber allows the face to be illuminated with diffuse light. An adhesive reference chart may be placed on the forehead of this person, during a process for calibrating the color of one or more cameras.

US 2003/0064350 A1 suggests giving personalized advise especially depending on the location of the individual to be advised.

There is a need to make it easier for as many people as possible to access personalized advice regarding the photoprotection to use in a given environment, especially depending on the pigmentation that it is desired to obtain and/or the pigmentation that has already been obtained.

In addition, many people would like to know which natural skin colors are likely to be damaged by the pigmentation process, in order to help decide, for example, between a relatively long exposure to the sun and/or the use of compositions intended to temporarily modify the color of the skin and giving the skin a color obtainable via the pigmentation process.

The invention meets all or some of these requirements by virtue of a cosmetic method, especially for providing help choosing a photoprotective composition or a product intended to temporarily modify the color of the skin, in which:

a) a color is acquired from a region of the body of an individual, by using a device equipped with a color camera and by placing a color reference chart in the field of said camera during the acquisition; and b) using the device, and the color acquired in a), and optionally knowledge of the tanning pathways of various skin colors, at least one indication is delivered concerning skin type and/or an indication is delivered concerning at least one skin color obtainable by the individual via the pigmentation or depigmentation process and/or at least one indication is delivered concerning photoprotection, especially UV-A and/or UV-B photoprotection, and/or application or administration of a product intended to temporarily modify the color of the skin, the indication(s) preferably being delivered automatically.

The expression "pigmentation obtained" is, unless otherwise stated, understood to mean the result obtained from tanning.

The expression "pigmentation to be obtained" is, unless otherwise stated, understood to mean the result to be obtained from tanning.

The expression "pigmentation process" is, unless otherwise stated, understood to mean the tanning process.

Knowledge of the tanning pathway is not required in order to indicate the skin type but it is necessary to determine the one or more skin colors obtainable via the pigmentation process.

In a simplified variant the indication to be given concerning photoprotection may be based on skin type alone, but preferably the indication also takes account of additional information as detailed below, in order to provide precise and personalized advice.

By virtue of the invention, it is possible to carry out a precise measurement of the color of the skin using the low-cost color cameras of devices that are widely available to the public at the present time, such as smart phones or tablet computers.

In addition, these devices have a screen, memory, and sufficient processing capacity to rapidly run algorithms allowing an indication to be delivered concerning the one or more skin colors obtainable via the pigmentation process and/or the photoprotection to be applied.

Thus, the user may learn, by virtue of the invention, what their skin type is, and the device may be used to suggest photoprotection suitable for their sensitivity to UV rays.

In addition, the invention allows the sensitivity of the skin to the sun to be diagnosed empirically, and thus to avoid errors due to the use of a questionnaire.

The user may also learn what change in the color of their skin they can expect, and decide, depending on this information, on the result that they would like to obtain from the pigmentation process. The device may then provide advice on the photoprotection that should be used, for example, to obtain this result while screening as much as possible of the surplus UV radiation that is not needed to obtain this result.

As mentioned above, at least one indication concerning the application or administration of a product intended to temporarily modify the color of the skin may be delivered in step b).

Said product may be an oral or topical composition. Said product is, in a preferred variant, a food supplement and/or a self-tanning product. In a preferred variant, the product is a pro-pigmenting, depigmenting or anti-pigmenting product.

The invention also makes it possible, if it is desired, to provide an indication concerning, and especially to propose to the consumer, a makeup product to be applied. This makeup product may provide protection from the sun, and, optionally, it may be a colored solar protection product allowing a natural skin color to be obtained, i.e. a skin color lying on the tanning pathway of the user, or else allowing an unnatural skin color to be obtained in the case of very light skins that do not tan.

The use of a lightening composition may also be proposed to the user in step b), for example when said user desires to obtain a less pigmented skin color.

Advantageously, step a) is carried out at least once on skin that is not exposed to the sun. The method may comprises a step c) consisting in carrying out a second acquisition on another skin region, liable to have already been exposed to the sun, using the device and preferably again placing the color reference chart in the field of the camera.

The device may optionally be programmed to allow the user to indicate on which part of the body or face the acquisition is carried out, and this information and the result of the corresponding color measurement may be stored in the device, or on a remote server.

Knowledge of the part of the body or face used for the measurement may, if required, allow the colors obtainable via the pigmentation process to be predicted with greater precision by allowing tanning pathways specific to each region of the body to be employed.

Information concerning the actual pigmentation and/or photoprotection level already obtained by a region of the body or face, based on the color acquisitions carried out in a) and in c) and on knowledge of the tanning pathway for the unexposed skin color determined in a), may be delivered automatically via the device.

Thus, the user may decide to choose a potential photoprotective product depending on how much they would like to tan. For example, the user may decide to apply a photoprotective product in order to preserve an actual skin color, or because continued exposure to the sun is not expected to lead to a rapid and observable change in the color of their skin, there thus being no reason for additional exposure which in addition runs the risk of accelerating photoaging of the skin.

The device may provide the user with information regarding the photoprotection to use for each region of their body or face, the user simply having to measure the color of this region, preferably by using the color reference chart each time.

The device may be set up to ask the user to enter information on the length of time they will be staying in a given location, and the indication regarding photoprotection may be delivered by the device depending on this information regarding length of stay, for example after a server and/or local weather sensor, which the device may connect to automatically, have/has been consulted.

The sensor may deliver a result of a measurement of at least one item of weather-related data, preferably the ambient UV radiation strength. Using the result of the measurement delivered by the sensor advantageously removes any doubt regarding a weather forecast. All that is required is for the device to be connected, physically and/or by way of a data-exchange network, to said sensor. Details will be given below regarding various arrangements that can be envisioned for the sensor and device.

If required, the device may be set up to gather information regarding location and length of stay from an electronic calendar of the user, or from a service-provider site containing this information.

The information concerning the photoprotection to use may be sent to the electronic calendar of the user, for example to Google calendar or icalendar, in addition to being displayed on the screen of the device.

The device may be set up to deliver an indication regarding the photoprotection to use, for example, by displaying the SPF factor to use and/or the trade name of the composition to use and/or the UV-A protection factor, indicated in the form of abbreviations, logos, and/or a scale, optionally a color scale, and/or a factor representing protection from a natural and/or artificially generated part of the electromagnetic spectrum. The SPF factor to be used each day may be displayed for a number of days to come, for example the next three days at least. This information may be refreshed periodically as, for example, more accurate weather forecasts become available. If required, the device is informed of the brand of the photoprotective composition the user has at their disposal, and the indication delivered regarding the photoprotection to apply and/or the recommended length of exposure takes account of the UV screening properties of this photoprotective composition, which the user knows or may find out by accessing a database. If required, the screening properties are indicated by a code on packaging of the photoprotective composition, which code the device is able to decipher.

The device may also be set up to control a device such as the intelligent bottle described in publication US 2011/0247718 A1 by the Applicant, which bottle is capable of receiving signals that specify the mixture to be produced, in order to obtain a photoprotective composition with the desired photoprotection factor. In this case, use may be made of the capacity of the device to communicate wirelessly, for example via a Wi-Fi or Bluetooth connection.

Advantageously, the device is set up to ask the the user to enter information concerning the desired pigmentation level and/or skin color to be obtained and to deliver, at least based on this information, and preferably also based on knowledge of the weather to come, an indication regarding the photoprotection to apply. To help the user select the desired pigmentation level to be obtained, a number of skin colors may be displayed on the screen of the device, these skin colors corresponding to colors obtainable by the user via the pigmentation process, to within the color shift of the screen.

In order to minimize this color shift, the screen color may be calibrated. This calibration may advantageously be carried out at a point of sale of photoprotective compositions and/or products intended to temporarily modify the color of the skin. The user may also be encouraged, at the same point of sale, to download software that will subsequently allow them to measure the color of their skin, in the context of the implementation of the process according to the invention. The software which is downloaded may contain data for calibrating the screen. As a variant, the user calibrates the screen color themselves, using existing tools available from other sources. By way of example, mention may be made of the application "SpyderGallery™" and the probe "Spyder3™" from Datacolor allowing the color of an iPad screen to be calibrated.

Even when an uncorrected color shift does exist, the screen may provide the user with useful information, especially by allowing them to compare the displayed colors, which correspond to various levels obtainable via the pigmentation process. The actual skin color of the user may also be displayed and compared. Thus, it will be understood that the indication concerning the skin color obtainable via the pigmentation process capable of being delivered in step b) must not be understood as limited in scope and encompasses situations where the color displayed corresponds to the actual color to within the ability of the screen to render the color accurately.

The device may ask the user to enter information regarding the desired skin color and deliver information on how it may be obtained, at least depending on the acquisition carried out in a) and preferably also depending on the acquisition carried out in c).

When the user is allowed to select a skin color, the device may be set up to determine, taking into account the items of information it has at its disposal, whether this color will be obtained, via the pigmentation process, by the end of a given period. For example, the device may take into account the length of stay in a given location, and the weather forecast for this location, in order to inform the user that the desired skin color will not be obtained by the end of the stay. In this case, the device may be set up to suggest using at least one composition intended to temporarily modify the color of the skin, especially a makeup, self-tanning, pro-pigmenting, depigmenting or anti-pigmenting product allowing the desired color to be obtained.

The device may also be used when the pigmentation obtained is gradually being lost once exposure to the sun has ceased, to measure, daily for example, the color of the skin and deliver advice to the user regarding a product intended to temporarily modify the color of the skin, to be applied or administered in order to preserve a natural skin color that is obtainable via the pigmentation process, especially a color selected by the user. In this case, the device may suggest, to a user having lost all or some of their previously acquired pigmentation, applying a makeup or pro-pigmenting composition, so that they may regain a color obtained previously via the pigmentation process.

Optionally the device may control an intelligent bottle such as that described in publication US 2011/0247718 A1, for example containing a neutral base and one or more coloring agents, in order to deliver a foundation with the color most suited to obtaining the desired appearance, especially in order to reproduce a natural color obtainable via the pigmentation process.

In one variant, the intelligent bottle controlled by the device delivers a self-tanning composition having a variable concentration, defined by the device, so as to obtain the desired skin color.

The device may also control an applicator that allows color to be varied, for example an airbrush or an ultrasonic or electrostatic spray gun, so that this applicator delivers the color allowing the result desired by the user to be obtained.

The device may have the color characteristics of a plurality of compositions intended to temporarily modify the color of the skin, especially makeup, and capable of being used to obtain an optionally tanned skin color, stored in memory, or may be able to access a database containing this information.

All the calculations can be performed by the device and all the data required to perform these calculations, and the information stored in memory following the various measurements, may be contained in the device.

However, as a variant, some of the calculations may be performed by a remote server external to the device, to which the latter transmits the information required to perform these calculations, before receiving in turn the result of these calculations. The ability of the device to communicate is then advantageously used to exchange this information.

As another variant, data is collected and/or saved on a remote server, while a program is being run on the device.

The device is used to measure the color of bare skin, but it may also be used to measure the color of madeup skin in order to provide the user with information concerning, for example, how suited an applied makeup composition is to their skin color. For example, the device may signal to the user that the makeup that they are wearing gives their skin a color that is relatively different, colorimetrically, from a skin color obtainable via the pigmentation process. This information is, for example, delivered in the form of a numerical value and/or indications regarding ways in which to modify the color of the applied makeup in order to obtain a more natural skin color. This may help the user determine which foundation is likely to most suit their natural skin color.

The device may also ask the user about the cosmetic products they have at their disposal and, knowing the colorimetric properties of these compositions and the skin color of the user, generate makeup advice allowing them to match their natural skin color to a greater or lesser extent. The device may especially signal which product will allow a color most closely resembling a natural skin color to be obtained, by choosing, for example, from a range of products indexed by the device and/or by suggesting a mix of various indexed products, or by specifying commonly available food products and/or the proportions of mixtures of these products.

The invention also relates to a method, in which a quantity representative of a* (position on the red/green axis) is measured before and after exposure to the sun, and, depending on the difference, the presence or absence of erythema is determined. The measurement of a* may be carried out in step a) or c).

Another subject of the invention is a method in which, if erythema is detected, the device delivers a warning message and/or takes the erythema into account when recommending the photoprotective composition to apply.

The invention also relates to a color reference chart, especially for implementing the method according to the invention, comprising a window through which an acquisition of the color of the skin may be carried out, the chart preferably comprising at least three different gray levels and at least three different colors, and the chart also preferably being produced using non-metameric inks. The potential residual metamerism of the chart preferably results in an error in the measurement of the color of the skin under illuminants D65, A and CWL, which causes the device to consider that the skin is lighter than it actually is. The chart is described in more detail below.

The invention also relates to a computer software package for implementing the method, comprising data allowing, when loaded, preferably by way of a connection to a remote server, into a device, such as a smart phone or a tablet computer, equipped with a camera:

the acquisition of the image of a chart placed on the skin to be controlled;

the color reference chart and a region of skin adjoining this chart to be recognized;

the acquisition units of the device to be colorimetrically calibrated via knowledge of the absolute color coordinates of the chart; and an indication concerning skin type and/or an indication concerning at least one individual skin color obtainable via the pigmentation or depigmentation process and/or an indication concerning application or administration of a product intended to temporarily modify the color of the skin and/or a photoprotection to be applied, to be generated, based on knowledge of the skin color measured in the image and optionally on knowledge of tanning pathways. This skin color may optionally be read from a scale bar comprising a skin-color scale, provided on the packaging of a cosmetic product of a brand indicated by the software package.

Such a program is, for example, downloaded from sites such as Apple Store, Windows Store, or Android Market, or is provided on an optical disk or electronic memory.

BRIEF DESCRIPTION OF DRAWINGS

The invention may be better understood on reading the following detailed description of non-limiting illustrative embodiments thereof and on examining the appended drawings, in which:

FIG. 3 shows an exemplary packaging and distribution unit provided with a chart;

FIG. 3a shows an assembly comprising a protective cover, a device and a chart;

FIGS. 4 and 5 show examples of the format in which the charts may be packaged;

FIG. 10 illustrates how an intelligent bottle may be controlled using the device.

Figure 1:
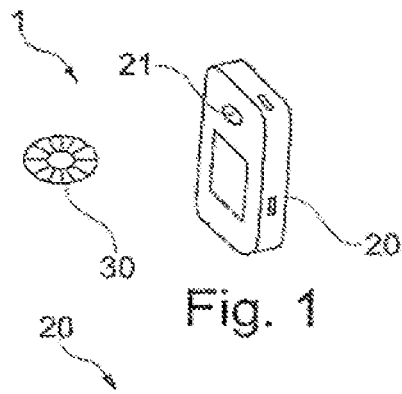
FIG. 1 shows, schematically, an example of a system for implementing the invention.

The system 1 according to the invention, shown in FIG. 1, comprises a portable device 20 and a color reference chart 30, which will now be described in succession in detail.

Color Reference Chart

Figure 2:
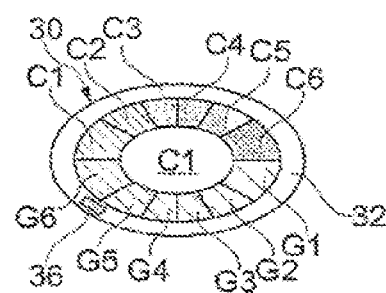
FIG. 2 shows the color reference chart in isolation.

A nonlimiting example of a chart is shown in FIG. 2.

The chart comprises at least one zone, and preferably a plurality of zones, the color coordinates of which are known with precision in a reference color space, preferably the CIE (1976) L*a*b* color space.

Preferably, the chart is produced in order to be as insensitive as possible to different illuminants, and may thus be produced using dies that are weakly metameric or non-metameric, especially with respect to standard CIE illuminants D65, A and CWL.

Preferably, the color reference chart comprises at least three different gray levels $G_1, \ldots, G_n$ and at least three different colors $C_1, \ldots, C_m$, and preferably at least six gray levels and six colors, for example two flesh colors, two blues, a red and a green.

The gray levels and colors may each take the form of a sector, all the sectors together advantageously forming a complete circumference.

The sectors or other colored or gray portions may adjoin or be separated by black strips, for example.

As illustrated in FIG. 2, the chart preferably comprises a window 31 which is advantageously located centrally. The acquisition of the color of the skin is carried out using the device by observing the skin, preferably through the window 31.

The external outline of the chart is for example substantially circular, as illustrated, but the invention is not limited to a chart having a particular shape, and the chart may have a polygonal shape, for example.

The largest dimension of the chart, for example its external diameter in the case of a circular chart, as illustrated, is for example smaller than or equal to 5 cm, and is preferably between 2 and 4 cm, so that it can be easily positioned on various regions of the body or face.

The window 31 is preferably larger than 0.5 cm² in size, and is preferably between 1 and 5 cm² in size, in order that a large enough area of skin is visible for an accurate measurement to be possible.

The window 31 may be bounded by a circular aperture, as illustrated; however, as a variant, the window may have a noncircular outline, for example having a polygonal outline or an outline with some other shape.

The color reference chart 30 may be produced on any medium 32, but is preferably produced on a flexible medium, for example on paper, by printing. The inks used are preferably non-metameric inks, so as to make the chart sufficiently illuminant-insensitive, especially to illuminants D65, A, and CWL. The medium 32 is preferably opaque or white before printing, which may be carried out by flexographic, offset or digital printing. The medium may be made of paper, cardboard or preferably of a synthetic material such as a polyolefin, especially PE or PP. The thickness used will for example be from 30 µm to 2 mm.

In one embodiment, the color L*a*b* coordinates of the various regions of the chart are the following:

| ColorChecker | | | | |
|---|---|---|---|---|
| No. | Name | L* | a* | b* |
| 1 | dark skin | 37.986 | 13.555 | 14.059 |
| 2 | light skin | 65.711 | 18.13 | 17.81 |
| 3 | blue sky | 49.927 | −4.88 | −21.925 |
| 4 | red | 42.101 | 53.378 | 28.19 |
| 5 | green | 55.261 | −38.232 | 31.37 |
| 6 | blue | 28.778 | 14.179 | −50.297 |
| 7 | white | 96.539 | −0.425 | 1.186 |
| 8 | gray 1 | 81.257 | −0.638 | −0.335 |
| 9 | gray 2 | 66.766 | −0.734 | −0.504 |
| 10 | gray 3 | 50.867 | −0.153 | −0.27 |
| 11 | gray 4 | 35.656 | −0.421 | −1.231 |
| 12 | black | 20.461 | −0.079 | −0.973 |

It has been demonstrated that it is possible to produce the chart in such a way that the error in the ITA° angle calculation, resulting from the variation in the skin color measured as a function of the illuminant, remains relatively small. Preferably, this variation ΔE is smaller than 2 when an inspection is carried out with a spectrocolorimeter.

In particular, it is advantageous for the difference between the ITA° measured with the camera and the chart to be smaller than the ITA° calculated using a more precise spectrophotocolorimeter measurement. Thus, the error leads to overprotection of the skin rather than underprotection, which is advantageous with respect to decreasing the risk of erythema.

That side of the chart to be applied to the skin may be adhesive, for example by virtue of the use of a medium coated with a pressure-sensitive adhesive. The adhesive is hypoallergenic. As a variant, the side making contact with the skin is non-slip, by virtue for example of the use of a rough, for example cellular, material. A notch or tab may be provided, if required, to make unsticking the chart easier.

If required, the chart may be washable, in order to be reusable.

The chart may be provided to the user with the photoprotective composition, for example in the same package, or adhesively bonded on top with a repositionable adhesive, as illustrated in FIG. 3. As a variant (not shown) the chart is fastened, especially adhesively bonded, to the cap, and not to the body, of the container containing the photoprotective composition. The chart may also be provided in the same package as a digital medium on which a program is stored, allowing the device to execute the algorithms required to implement the invention.

FIG. 3a shows a variant in which the chart 30 is provided to the user with a casing 22 for protecting the device, the latter being a smartphone or a tablet computer, for example. The chart 30 and the casing 22 may, as illustrated, be provided to the user in the same packaging 50. The chart 30 may be configured so as to be able to be fastened to the casing 22, for example by adhesive bonding, and to be able to be separated therefrom at the moment of use.

A plurality of self-adhesive charts 30 may be provided to the user, these charts being bonded to the same anti-adhesive supporting sheet 34, as illustrated in FIG. 4.

Thus, the user may use a new chart when the preceding chart is no longer sticky enough to adhere to the skin for enough time to make the measurement.

If required, the anti-adhesive supporting sheet 34 takes the form of a strip, as illustrated in FIG. 5, and may be contained on a reel.

The chart may comprise an identifier 36 or a hyperlink or a barcode allowing the device to recognize the chart or the user to download an application allowing the chart to be used. As a variant, this identifier, link or barcode is present in a package in which the chart is contained.

Recognition of the chart by the device may be useful when there are a number of charts on the market with different properties.

In this case, since the device recognizes the chart, it may access the relevant color data.

As a variant, the chart comprises a code that directly informs the device of the color coordinates of the various regions of the chart. This is, for example, a Data Matrix 2D barcode encoding the color coordinates, for example the color coordinates measured after printing of the chart.

As a variant, the chart may comprise a security element. In this case, the device may be configured to recognise the signal produced by said security element present in the chart and thus permit, when said signal is detected, the method according to the invention to be implemented. The device may, of course, be configured to prevent the method according to the invention from being implemented when said signal is not detected. The presence of a security element may also allow a user to check the authenticity of the chart, for example by looking for a visible optical effect produced by the security element present in the chart.

Among the security elements that may be incorporated in the chart, certain security elements can be detected with the naked eye, under sunlight or artificial light, without any particular apparatus being used. These security elements for example comprise colored fibers or flakes, or partially or completely metallized or printed threads. These security elements are what are called level one security elements.

Other types of additional security elements can only be detected using a relatively simple device such as an ultraviolet (UV) or infrared (IR) lamp. These security elements for example comprise fibers, flakes, strips, threads or particles. These security elements may be visible or invisible to the naked eye, being, for example, luminescent under illumination from a Wood's lamp emitting at a wavelength of 365 nm. These security elements are what are called level two security elements.

The detection of other types of security element requires the use of a more sophisticated detection device. These security elements are for example capable of generating a specific signal when they are subjected, simultaneously or otherwise, to one or more external excitation sources. The automatic detection of the signal allows the chart to be authenticated, if required. These security elements for example comprise tracers taking the form of active materials, particles or fibers capable of generating a specific signal when these tracers are subjected to optronic, electric, magnetic, or electromagnetic excitation. These security elements are what are called level three security elements.

Reactive agents may also be incorporated in the chart, these are for example reactive chemical or biochemical agents allowing authentication and/or identification and/or for preventing counterfeiting, the agents being able to react, respectively, with, in particular, at least one agent allowing authentication and/or identification and/or for preventing counterfeiting.

The one or more security elements present in the chart may be level one, level two or level three security elements.

Although it is preferable for the chart to be independent of the device, the chart, in variant embodiments that are not illustrated, may nevertheless be connected to the device, either by being removably attached to a casing of the latter, or to a retractable element that is securely fastened to the jacket of the device, which element is extracted to carry out the measurement and then replaced afterwards.

The chart may be coated with a mat or gloss varnish that protects from UV.

Device

The device 20 is preferably a smartphone.

The device is thus preferably equipped with a wireless telephony function allowing it to download a software package that is then run on the device, or to download data needed by the software package to implement the method according to the invention.

The device may also comprise a housing for receiving a memory card, which card may contain the program to be executed. This card may have been supplied with the chart, as indicated above.

The device comprises a high- or low-resolution color camera 21, for example with more than 1 Mpixels, and may optionally have an autofocus and/or an optical zoom function.

The device also has a color screen and a keyboard, the screen possibly being a touchscreen.

The device is for example an iPhone, sold by Apple Inc, or a mobile telephone using an Android or Windows operating system or another operating system.

The program run when the invention is implemented may have been pre-installed on the device or may be downloaded subsequent to its purchase by the user.

The program may be downloaded by connecting to a server or by introducing a data medium, such as a memory card, for example a micro SD card, containing the program to be executed, into the device. The download may, if required, be carried out at a point of sale by way of a short-range connection, for example a Bluetooth or Wifi connection.

When the program must be downloaded by the user, it is possible for the download to take place after the user has answered a questionnaire, for example concerning the type of device used, their skin type, their age, their gender, and their habits in terms of use of cosmetic products or outdoor activities.

The program transferred to the device may depend on the responses to this questionnaire and especially on the make of the device that will receive the program. This is advantageous because it allows the technical features of the camera of the device to be taken into account during the acquisition, and the instructions given to the user to be matched to the nature of the device and to its capabilities.

Figure 8A:
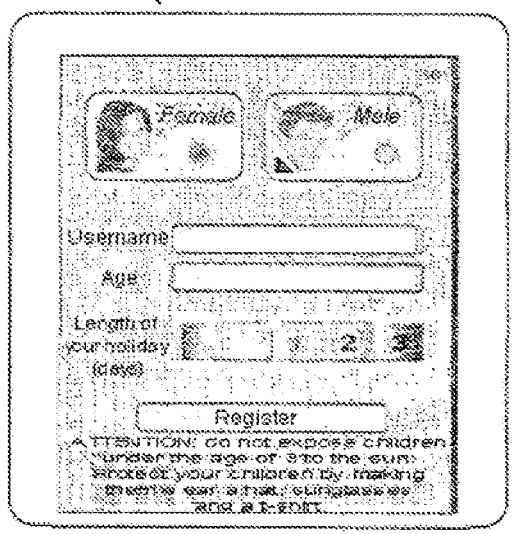
FIGS. 8A to 8G show examples of screen pages that may be displayed when the program is being run by the device.

If required, the aforementioned questionnaire is displayed when the program run by the device is initiated, as illustrated in FIG. 8A.

The device may also be provided with a geolocation function, for example a GPS chip. As a variant, the geolocation function is ensured by the telephone network. The location and the weather forecast may be displayed by the device in the context of execution of the program, as illustrated in FIG. 8D.

The device does not need to comprise a UV radiation sensor. However, preferably, the device may automatically access a weather-forecast server that provides it with information on the weather to come in the location where the user will be, and optionally on the strength of UV radiation.

In an exemplary embodiment, the device may be connected to a sensor allowing the strength of ambient UV radiation to be measured. In this case, the sensor may be present on the device or even on a casing of the latter. It may even be envisioned for the sensor to be carried by the user themselves, for example on their wrist.

The device need not be a smartphone, it may for example be a tablet computer, for example an iPad2 or another tablet PC, a smart digital camera, a portable computer equipped with a webcam, or a portable digital music player, for example an iPod. More generally, any device comprising a camera and able to run a software package may be used.

Preferably, the device fits in the hand, which makes it easier to handle during acquisition of the images of the chart placed on the skin.

Measuring Process

Figure 6:
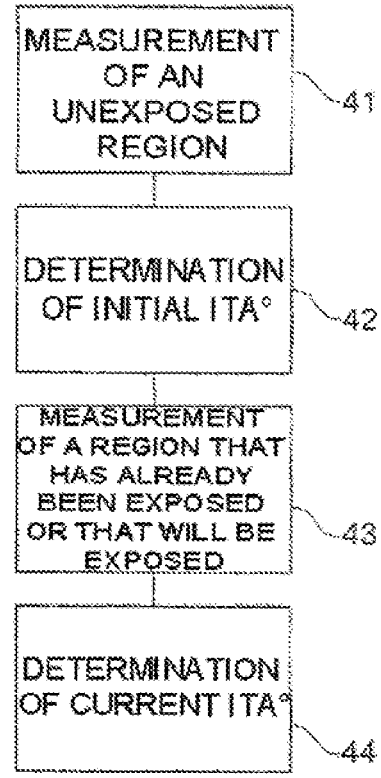
FIG. 6 is a flow chart illustrating various steps in an example of a method according to the invention.

Various steps of an example of a measuring process are illustrated in FIG. 6.

To obtain the measurements, a region of skin free from blemishes, i.e free from beauty spots, scars, wounds, hair, and protruding blood vessels, is selected.

According to one variant of the invention, the color of the skin is measured in at least one region that is not normally exposed to the sun, in order to obtain a reference skin color, which corresponds to step 41 in FIG. 6. Additionally, the color of the skin may be measured in a region that has already been exposed. The user may be asked by the device to choose, as illustrated in FIG. 8B, what type of measurement they would like to carry out, for example measurement of unexposed skin, i.e. "initial ITA°" or measurement of previously exposed skin, i.e. "current ITA°".

The normally unexposed region is typically a region that is not exposed because clothing is worn over it, or because of its orientation. It may for example be the upper part of the arm, the stomach, the breasts or buttocks.

To carry out the acquisition, the user places the chart 30 on this region and takes a photograph of the chart or films it. It may be advantageous to take a number of photographs or to film said region in step a).

The user preferably ensures that the image is clear and includes the colors and gray regions of the chart. If required, the device automatically performs this check, and sounds an alarm if the image is unsuitable for the measurement.

The program run by the device determines parameters for color conversion tables allowing, for example, RGB signals delivered by the camera for the various regions of the chart to be converted into the absolute color coordinates in the CIE L*a*b* space known by the device for these regions.

If required, in the case where a number of charts are available on the market, it may be necessary to communicate a chart identifier to the device beforehand, so that the device knows what colors the various regions correspond to. For this purpose, the chart may contain an identifier 36, which is deciphered by the device.

Once the color acquisition units of the device 20 have been calibrated, the color of the skin in the image, for example in a window 31 in the chart the outline of which window can be easily detected in the image, can be measured.

For example, an average color is determined over all of the skin pixels observed through the window 31. This allows the color coordinates L*, a* and b* to be found for the skin and, in step 42, the ITA° angle of the unexposed skin to be calculated by applying the formula given above, established by A. Chardon.

Figure 7:
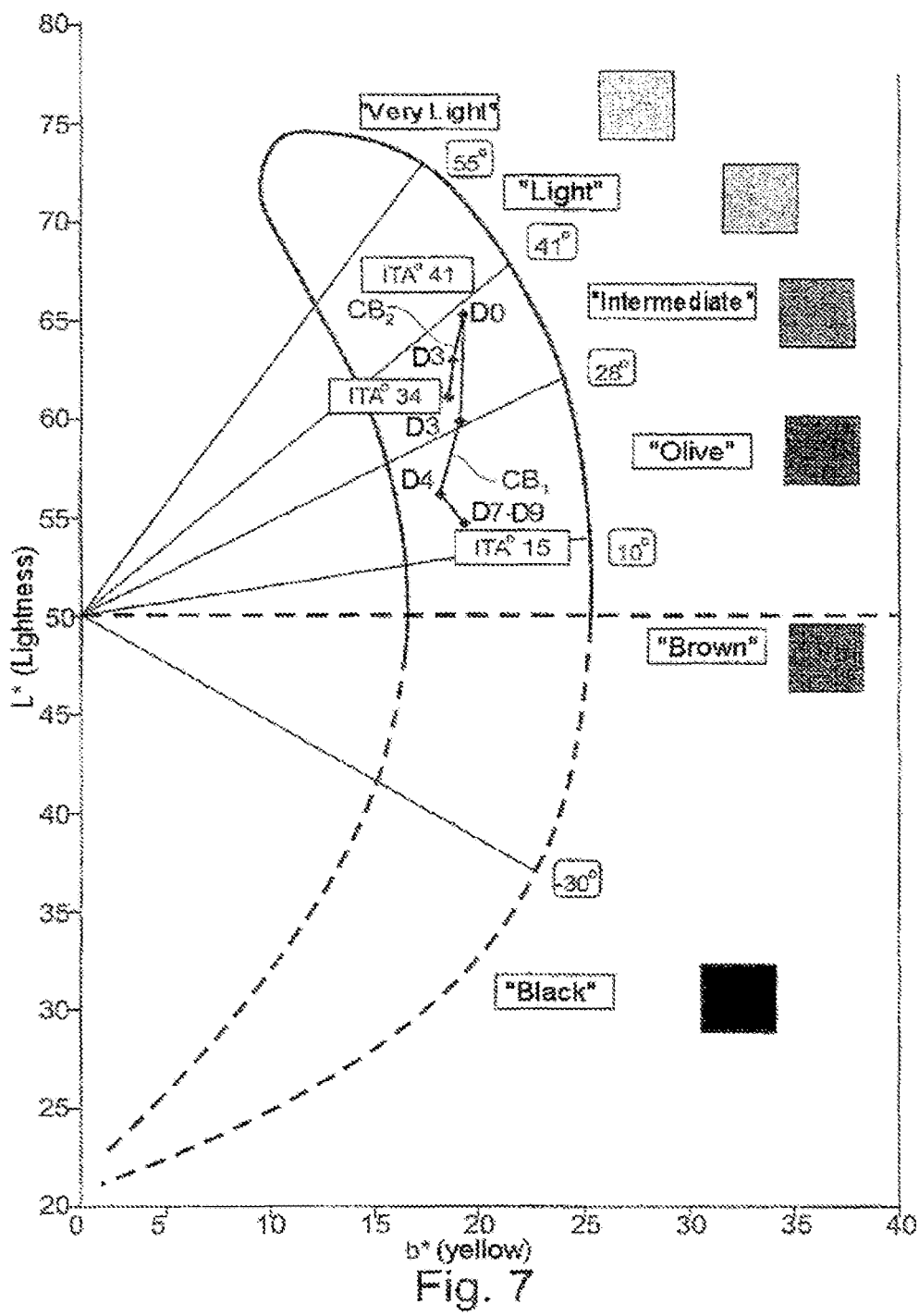
FIG. 7 shows an example of a tanning pathway as represented by A. Chardon.

Knowing the ITA° angle of the unexposed skin, it is possible to determine the skin type, as illustrated in FIG. 7, and optionally to indicate it to the user. For example, the device displays "very light skin" for an angle larger than 55°, "light skin" for 41°<ITA°<55°, "intermediate skin" for 28°<ITA°<41°, "olive-colored skin" for 10°<ITA°<28°, "brown skin" for −30°<ITA°<10°, or "black skin" for ITA°<−30°, and may also display the value of the ITA° angle.

Moreover, since tanning pathways L* (lightness) are known as a function of b* (position on the blue/yellow axis), it is possible to determine the change in L* as a function of b* during the pigmentation process for the skin in question, and to deliver a corresponding indication to the user.

Tanning pathways, two examples of which, denoted by the references $CB_1$ and $CB_2$, are shown in FIG. 7 for two different individuals having substantially the same initial ITA° angle, are known from studies among reference populations, as discussed in the article by A. Chardon mentioned above. In FIG. 7, the path taken before and/or after each day of tanning, D1 to D9, has been shown on each tanning path.

In a preferred variant, the device may be configured to measure and memorize, with a view to subsequent use, the actual tanning pathway of the user. This measurement may be carried out over a number of days spent tanning, for example 5 to 15 days spent tanning. During each day spent tanning, the user may apply a photoprotective composition of a known photoprotective power and proceed, at the end of the day, with an acquisition of the color value of their skin. Acquiring this color value over a number of days spent tanning will allow the actual tanning pathway of the user to be determined.

Knowledge and use, in the context of methods according to the invention, of the actual tanning pathway of the user may advantageously allow the indication delivered in step b) to be made more accurate.

Figure 9:
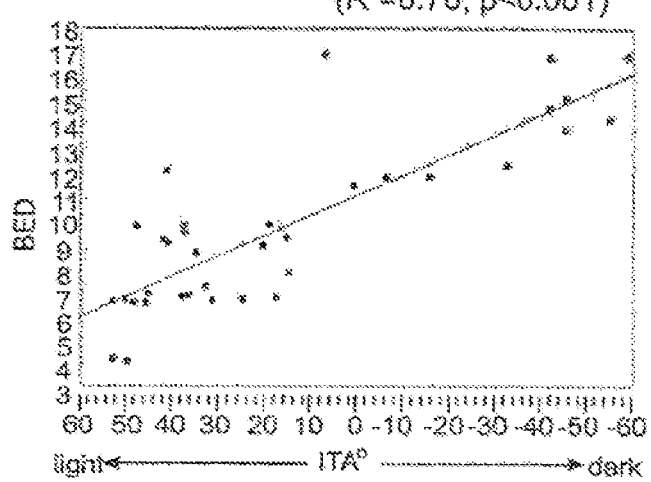
FIG. 9 shows an exemplary correlation between ITA° angle and biologically effective dose.

In order to determine the change in the ITA° angle as a function of exposure to the sun, a relationship giving the ITA° angle as a function of the biologically effective dose (BED) is used, which relationship is determined by experiments on reference populations, as illustrated in FIG. 9 after the article by S. Del Bino et al., *Relationship between skin response to ultraviolet exposure and skin color type*, Pigment Cell Res., Journal compilation 2006 Blackwell Munksgaard.

The received dose may be calculated based on UV radiation at a given location for given weather conditions and for a given activity. Knowledge of the activity may lead to the expected dose being reduced or increased; for example, if the activity involves lying in the sun without moving, the dose is maximized. If the activity involves playing a sport, which will presumably involve continuous changes in orientation relative to the sun, the dose will be lower than in the case of inactivity. Knowing the dose that the individual is liable to receive, it is possible to determine the corresponding change in the ITA° angle that would be observed if no photoprotection were used.

The measurement may be repeated in step 43 on a region of skin that has already been exposed to the sun, in order to determine, in step 44, the ITA° angle of the region considered and discover how far the pigmentation process has progressed.

The indication may be delivered to the user by displaying, on the screen, both the measured skin color and one or more skin colors obtainable via the pigmentation process, the latter colors being calculated using knowledge of the tanning pathway applicable to the skin for which the color has been measured.

The color of the screen is preferably calibrated, as explained above.

Figure 8C:
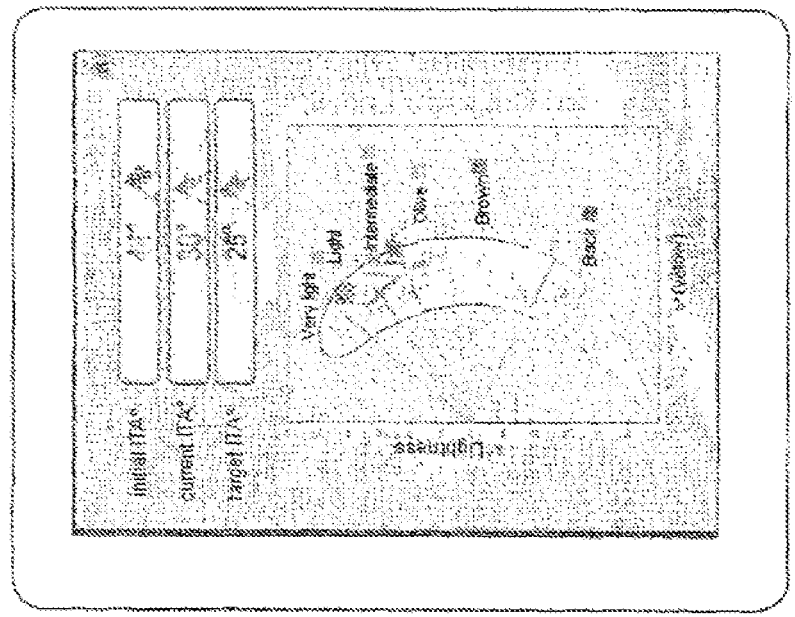
Figure 8B:
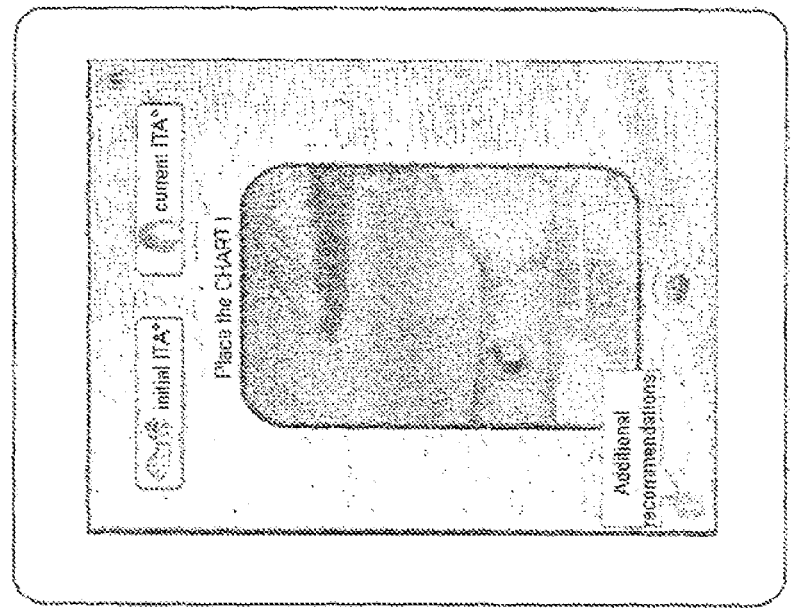
Figure 8E:
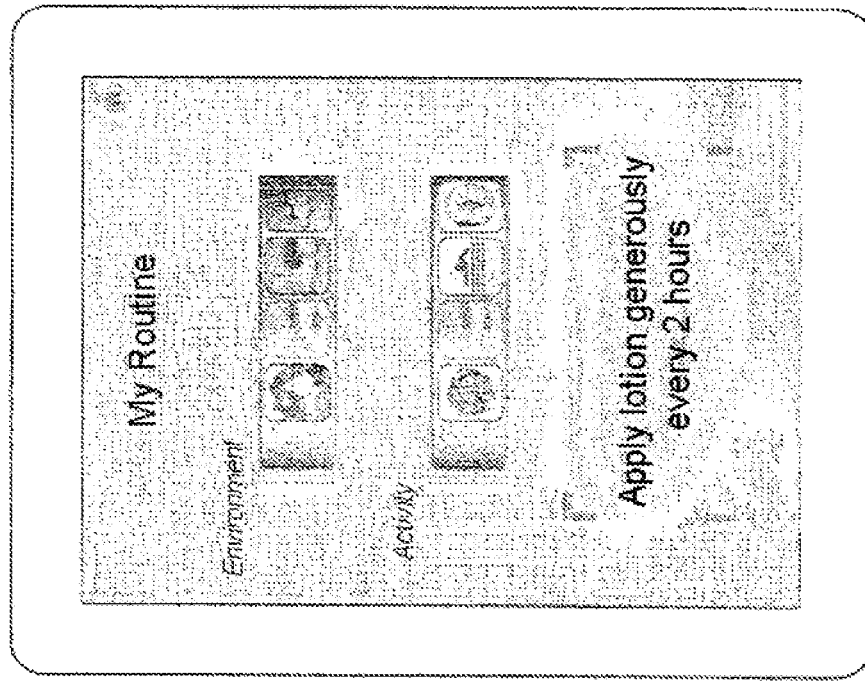
Figure 8D:
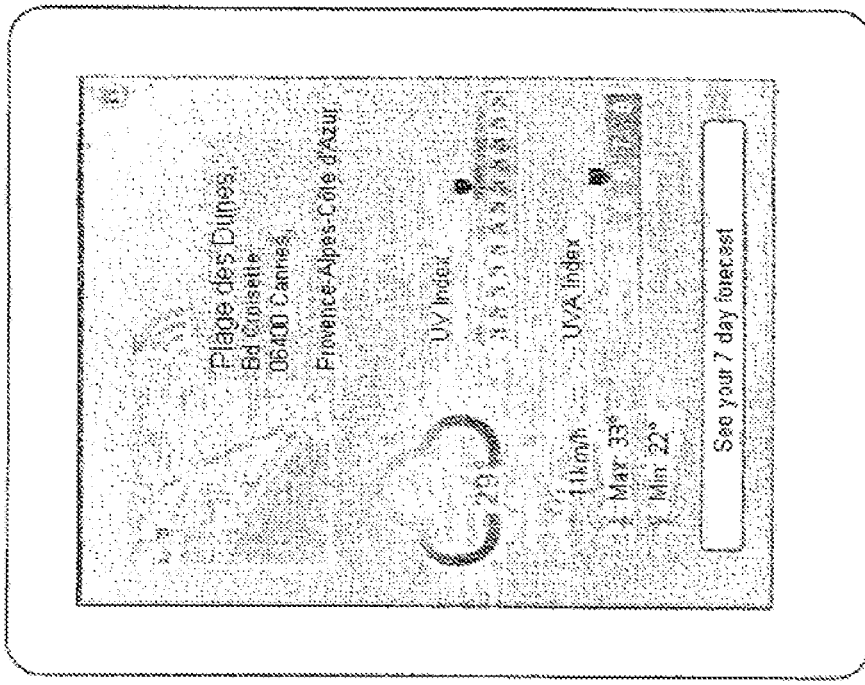
Figure 8F:
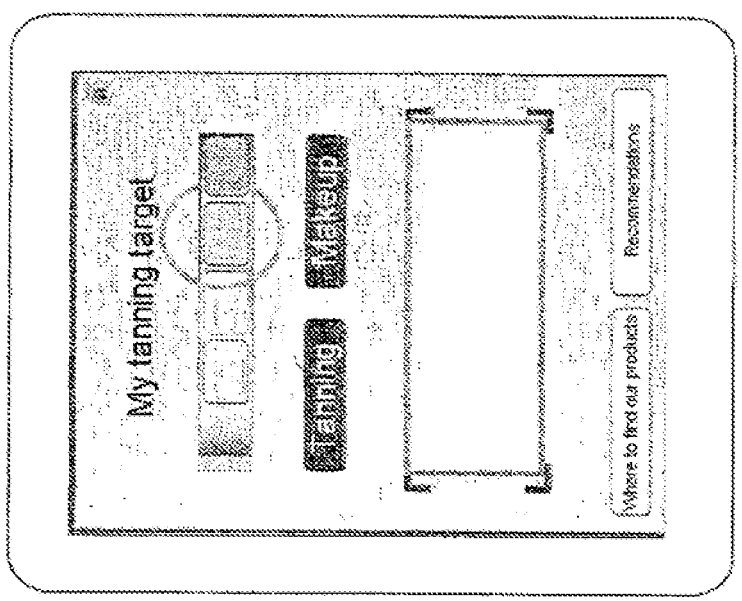

However, even if the screen color has not been calibrated, simultaneously displaying the one or more colors obtainable via the pigmentation process, as illustrated in FIG. 8F, nevertheless provides the user with information allowing them to see, by comparison, the possible changes in skin color available to them, despite the color drift of the screen.

In one variant, the device does not display this color, or in addition to displaying the color delivers information relating to an atlas of skin colors, thereby allowing the user to find, in the atlas, their skin color and those obtainable via the subsequent pigmentation process. Such an atlas, which is advantageously printed in a way that eliminates metamerism, may be present at a point of sale or be provided to the user with a cosmetic composition or with the chart or the program to be run by the device.

If required, the chart may contain one or more flesh colors, identified by identifiers, which correspond to colors to which the device may refer in order to allow the user to identify the color with more precision than is possible using the screen.

The method may comprise, as illustrated in FIG. 8F, a step consisting in asking the user to select that color, obtainable via the pigmentation process, which they would like to obtain.

For example, the device displays on the screen, as illustrated in this figure, colors on the tanning pathway of the user, and allows the user to select one color therefrom as the result to be obtained from the pigmentation process.

The device may furthermore ask the user for the length of time they will be staying at a given location, for example a holiday destination, and, based on this information, determine whether the pigmentation result selected by the user is feasible, without risking of erythema, in the amount of time allowed.

The device may determine the photoprotection to be applied based on knowledge of the incidence of the dose received on the color of the skin and on the appearance of solar erythema.

The program may also allow the user to measure the level of pigmentation acquired in any region of the body.

To do this, the user carries out an acquisition, using the chart, of the region for which they wish to know the acquired pigmentation level, for example the forehead. This assumes that the user has carried out an acquisition beforehand on an unexposed region, as detailed above.

Using the chart, an acquisition carried out on any region allows the ITA° angle to be calculated for this region and, assuming the ITA° angle of the unexposed region is known, allows, based on data known for the reference population, in this instance the reference population having the same original ITA°, the maximum ITA° angle that will be obtained at the end of the pigmentation process to be determined.

It is then possible to indicate to the user where they are on their tanning pathway, as illustrated in FIG. 8C, for example by showing extreme ITA° angles and the current ITA° angle.

This information may be delivered in various forms. For example, the device may deliver a message informing the user that their pigmentation level will not change much in certain regions of their body or face, which may encourage the user to avoid exposing them to the sun or to apply more protection to them.

The color measurement carried out on exposed regions may also be used, especially by virtue of the a* component on the red/green axis, to detect the appearance of potential solar erythema and to inform the user of the benefit of avoiding further exposure of such-and-such a region of the body or face to the sun until the inflammation reaction has disappeared.

The device may determine the presence or absence of erythema because the initial ITA° angle and a reference a* coordinate, measured by the device before exposure to the sun, are known. The device can compare the new measurement with the previously measured value and/or with the pigmentation that should have been acquired in the absence of erythema.

A change in a* smaller than a given threshold between two measurements may confirm that the individual has not developed an erythema and has correctly followed protection advice. In the case where erythema is detected, a warning message cautions the user to avoid further exposure to the sun.

If required, the device may, in the case where erythema is detected, take this into account when determining the photoprotective composition to be applied subsequently, for example by recommending the maximum photoprotection.

Figure 8G:
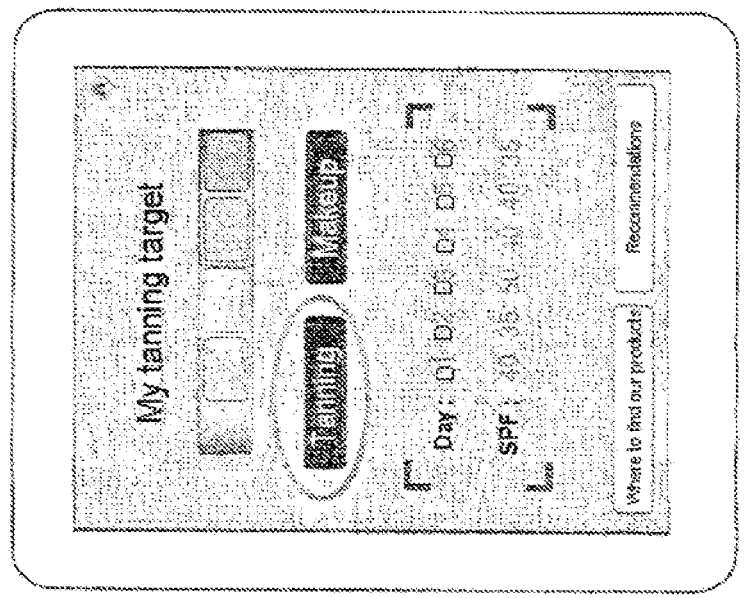

The device may be set up to suggest a makeup or self-tanning product that gives the user a skin color, which would have been obtainable via the pigmentation process, selected by the user, as illustrated in FIG. 8G. In this figure, the device displays two buttons allowing the user to select a recommended tanning product or a recommended makeup product.

The program may have, stored in memory, references to a number of products that may be applied to obtain such-and-such a skin color. The device may choose the product to be suggested to the user, if required, by way of a look-up table, stored in the memory of the device or accessible to the latter, comprising two data types, namely the color to be obtained and the current color, and for each of these pairs, one or more references to products listed as being likely to be suitable.

During the acquisition, or after the latter, the image may be analyzed to determine whether there are regions of very non-uniform color on the skin, and the device may take such regions into account in order to avoid using pixels attributed to color heterogeneities such as pimples, beauty spots, hairs or protruding blood vessels, when calculating the color of the skin. The device may also be set up to signal that an acquisition must be carried out in another zone, because of the presence of color inhomogeneities.

Photoprotection

The device may provide the user with information regarding the use of a photoprotective composition to be applied, with the aim of obtaining a skin color selected from among colors obtainable naturally via the pigmentation process.

The device may especially determine the SPF factor to be used depending on the pigmentation results that it is desired to obtain and on environmental factors such as UV radiation strength, activity undertaken, and the weather forecast.

The device may for example display a questionnaire allowing the user to indicate what activities they intend to undertake at various times of the day, as illustrated in FIG. 8E.

For example, a calendar is displayed by the device in which the weather forecast for various times of the day is displayed, and the user may indicate, for each of these moments, whether they will be in or out of doors, in the sun or under shade, in a highly reflective environment or not, active or inactive. This information may also be imported by the device from an electronic calendar where it has already been entered.

Next, the device calculates the maximum exposure liable to be received each day and generates a recommendation, for example by generating, on the calendar or on the welcome screen of the device, an icon indicating the solar protection factor to be used at each moment during the day, for example. In the example in FIG. 8G, the device indicates, for each of the days to come, the protection factor to be applied.

If required, the program triggers the emission of an audio, visual, or tactile signal at certain moments, to remind the user, for example, of the benefit of reapplying the photoprotective composition to certain regions.

At the end of the day, for example before the user goes to bed, the device may be used to carry out a new measurement in order to confirm the absence of erythema and, in the case where erythema is detected, make a recommendation to the user regarding the days to come, for example advising them not to expose the region concerned or to change to a higher protection factor. The device may also advise the application of a suitable soothing product, once erythema has been detected.

As indicated above, the device may be set up, as illustrated in FIG. 10, to communicate with what is called a smart container/applicator 100, for example by virtue of a wireless link between the device and said container/applicator.

For example, this container/applicator has two compartments containing products with different protection factors and a mixer allowing the contents thereof to be mixed in chosen proportions, in order to obtain the desired protection factor, such as described, for example, in application US 2011/0247718 A1.

In this case, the device may automatically deliver set point data to the container/applicator allowing a composition with a suitable SPF to be obtained.

In a variant, the photoprotective composition is contained in a bottle equipped with an identifier, for example a bar code, that can be recognized by the device, using the camera.

The device may then identify the photoprotective composition which the user has at their disposal and, knowing this, give advice regarding its use, for example recommending an application frequency or signaling that the factor of the composition used will only allow the user to stay in the sun for a certain amount of time before they risk suffering from erythema.

The device may signal to the user, if required, that they may expose themselves to the sun or that it is time for them to cover themselves or get into the shade. The user may signal the moment when their exposure starts, in order to allow the device to then generate an alarm, by calculating the length of the exposure and the dose received, when there is a risk of erythema.

The program run by the device is advantageously a multi-user program, thereby allowing a number of people to identify themselves and use the device one after the other while retaining the benefit of previous sessions.

The invention is not limited to the examples that have just been described.

For example, the acquisition of the initial ITA° angle of unexposed skin may be carried out at a point of sale using a dedicated device. Next, the individual may use their smart phone to measure the pigmentation level obtained, without once more having to carry out an acquisition in an unexposed region, by downloading an application from a server to which the data acquired at the point of sale will have been communicated.

As yet another variant, the user employs a computer equipped with a webcam, and a chart that they have obtained, for example, from their travel agent or hotel. The result of the acquisition is sent to a remote site that generates advice regarding photoprotection, for example by indicating the factor that each member of the family should use and the pigmentation that each member is liable to obtain, depending on a given activity program, for example proposed by the agent or hotel.

The tanning pathway may be determined in a color space other than the CIE L*a*b* space.

Skin type may be determined by calculating a quantity other than the ITA° angle.

The expression "comprising a" should be understood to be synonymous with "comprising at least one".

The invention claimed is:

1. A cosmetic method in which:
a) acquiring a color from a region of the body of an individual, by using a device having a color camera, memory, and a processor and by placing a color reference chart in the field of said camera during the acquisition, and acquiring an image of the chart, wherein the color reference chart and a region of skin adjoining the chart are recognized by the device, the color camera being colorimetrically calibrated via knowledge of absolute color coordinates of the chart; and
b) delivering automatically by the device using the color acquired in a) by the color camera and knowledge of tanning pathways of various skin colors stored in the memory or to be downloaded into the device,
at least one data representative of skin type of the individual,
at least one indication concerning at least one skin color obtainable by the individual via a pigmentation or depigmentation process, and
at least one indication concerning photoprotection and/or application or administration of a product intended to temporarily modify the color of the skin, to be applied to obtain a skin color that is the same as one of the at least one skin color obtainable by the individual via the pigmentation or depigmentation process.

2. The method as claimed in claim 1, in which step a) is used to measure the skin color of a region that is not exposed to the sun or to an exogenous or endogenous stimulus inducing pigmentation or depigmentation.

3. The method as claimed in claim 2, in which the measurement carried out on the unexposed region is used to determine the skin type.

4. The method as claimed in claim 2, in which:
c) a second acquisition is carried out on another skin region, liable to have already been exposed to the sun, using the device, wherein the second acquisition is carried out placing the color reference chart in the field of the camera.

5. The method as claimed in claim 4, in which information is automatically delivered with said device, the information concerning the pigmentation and/or photoprotection level already obtained by this other region, based on the color acquisitions carried out in a) and c) and on knowledge of tanning pathway.

6. The method as claimed in claim 1, in which the individual is asked to enter, into the device, information concerning the desired pigmentation level and/or skin color to be acquired and, at least on the basis of the information entered into the device, an indication is delivered on the photoprotection to be applied, in which the individual is asked to enter information on the length of time they will be staying in a given location, and in which the indication regarding photoprotection is delivered depending on this information regarding length of stay.

7. The method as claimed in claim 4, in which the individual is asked to enter information on the desired skin color, and in which the device delivers information, depending at least on the acquisition carried out in a) and in c), regarding the way to obtain it via the pigmentation process or via application or administration of a product intended to temporarily modify the color of the skin.

8. The method as claimed in claim 1, the device being portable and comprising a screen, and the device being equipped with a wireless telephone and/or computer connection.

9. The method as claimed in claim 1, in which the at least one indication delivered by the device concerns one or more products and/or combinations of products or instruments intended to temporarily modify skin color, to be applied or administered to obtain a skin color corresponding to a real skin color of the individual that may be obtained via the pigmentation process, said at least one indication being determined via knowledge of an unexposed skin color, of the individual and of tanning pathway.

10. The method as claimed in claim 1, in which a program is downloaded before the color acquisition is initiated, this program allowing the device to carry out the color acquisition and to provide the one or more indications concerning the skin type and/or concerning the one or more skin colors that are obtainable via the pigmentation or depigmentation process and/or concerning application or administration of the product intended to temporarily modify the color of the skin and/or concerning the photoprotective composition to be applied.

11. The method as claimed in claim 1, in which the device automatically determines its geographical location and takes it into account to determine a predicted level of daily solar exposure and/or a photoprotection to be applied and/or to predict a change in pigmentation to be acquired day by day.

12. The method as claimed in claim 1, in which the device automatically consults a server that provides it with a weather forecast and/or is connected to a sensor providing it with the result of a measurement of at least the ambient UV radiation strength, said device taking this forecast and/or the result of this measurement into account in order to evaluate a change in pigmentation to be acquired and/or a photoprotection to be applied, or in which the device asks the individual to select an activity and takes account of the activity selected to suggest a photoprotection and/or to determine the change in pigmentation to be acquired.

13. The method as claimed in claim 1, in which the device delivers said indication concerning at least one skin color that is obtainable via the pigmentation process by displaying this color on a screen and simultaneously displaying, on the screen, a current skin color of the individual in an unexposed region and/or in another already exposed region and where a color acquisition has also been carried out.

14. The method as claimed in claim 1, in which the ITA° angle is calculated on the basis of the color acquisition, and the ITA° angle is used to determine the skin type and/or tanning pathway.

15. The method as claimed in claim 1, in which a quantity representative of a* is measured before and after exposure to the sun, and, depending on the difference, the presence or absence of erythema is determined and in which, if erythema is detected, the device delivers a warning message and/or takes the erythema into account when recommending a photoprotective composition to apply.

16. A system for implementing a cosmetic method comprising:
   a color reference chart, and
   a portable device equipped with memory, a processor, and a color camera colorimetrically calibrated via knowledge of absolute color coordinates of the chart, the device being configured to:
      acquire a color from a region of a body of an individual by acquiring an image of a region of skin with the color reference chart being in the field of the camera during the acquisition, and
      deliver, based on the color acquired by the color camera and knowledge of tanning pathways of various skin colors stored in the memory or to be downloaded into the device,
   at least one data representative of skin type of the individual,
   at least one indication concerning at least one skin color obtainable by the individual via a pigmentation or depigmentation process, and
   at least one indication concerning photoprotection and/or application or administration of a product intended to temporarily modify the color of the skin, to be applied to obtain a skin color that is the same as one of the at least one skin color obtainable by the individual via the pigmentation or depigmentation process.

17. A non-transitory computer readable storage medium storing a computer-executable program that causes a computer to perform functions comprising:
   controlling an acquisition of an image of a color reference chart placed on a skin of a body of an individual by a device;
   acquiring a color from a region of the body of the individual from the image, the acquisition units of the device being colorimetrically calibrated via knowledge of the absolute color coordinates of the chart; and
   delivering, based on the acquired color and knowledge of tanning pathways of various skin colors,
   at least one data representative of skin type of the individual,
   at least one indication concerning at least one skin color obtainable by the individual via a pigmentation or depigmentation process, and
   at least one indication concerning photoprotection and/or application or administration of a product intended to temporarily modify the color of the skin, to be applied to obtain a skin color that is the same as one of the at least one skin color obtainable by the individual via the pigmentation or depigmentation process.

* * * * *